United States Patent [19]
Le Count et al.

[11] 4,059,622
[45] Nov. 22, 1977

[54] ALKANOLAMINE DERIVATIVES

[75] Inventors: David James Le Count; Christopher John Squire, both of Macclesfield, England

[73] Assignee: Imperial Chemical Industries Limited, London, England

[21] Appl. No.: 445,854

[22] Filed: Feb. 26, 1974

Related U.S. Application Data

[63] Continuation-in-part of Ser. No. 431,297, Jan. 7, 1974, Pat. No. 3,959,486, which is a continuation of Ser. No. 145,897, May 21, 1971, abandoned, and a continuation-in-part of Ser. No. 332,517, Feb. 14, 1973, abandoned.

[30] Foreign Application Priority Data

| | | |
|---|---|---|
| May 27, 1970 | United Kingdom | 25529/70 |
| Nov. 20, 1970 | United Kingdom | 55246/70 |
| Mar. 21, 1972 | United Kingdom | 13159/72 |

[51] Int. Cl.$^2$ ............... C07C 103/26; A61K 31/165
[52] U.S. Cl. ............... 260/559 A; 260/501.17; 424/324
[58] Field of Search ............... 260/501.17, 559 A; 424/324

[56] References Cited

U.S. PATENT DOCUMENTS

| | | | |
|---|---|---|---|
| 3,175,006 | 3/1965 | Druey et al. | 260/501.17 X |
| 3,328,424 | 6/1967 | Schenker et al. | 260/501.17 X |
| 3,466,325 | 9/1969 | Brandstrom | 260/501.17 |
| 3,483,221 | 12/1969 | Wilhelm et al. | 260/326.14 |
| 3,562,297 | 2/1971 | Howe et al. | 260/562 |
| 3,574,749 | 4/1971 | Howe et al. | 260/562 |
| 3,634,511 | 1/1972 | Howe et al. | 260/562 |
| 3,663,607 | 5/1972 | Barrett et al. | 260/501.17 |

FOREIGN PATENT DOCUMENTS 2,126,169   12/1971   Germany ............... 260/559

Primary Examiner—James O. Thomas, Jr.
Assistant Examiner—G. T. Breitenstein
Attorney, Agent, or Firm—Cushman, Darby & Cushman

[57] ABSTRACT

New 1-amino-3-(o-carbamoylalkoxyphenoxy)propan-2-ol derivatives, for example 1-t-butylamino-3-(o-N-methylcarbamoylmethoxyphenoxy)propan-2-ol, processes for their manufacture and pharmaceutical compositions containing them. The compounds possess $\beta$-adrenergic blocking activity and are useful in the treatment of heart diseases and other conditions in man.

3 Claims, No Drawings

ALKANOLAMINE DERIVATIVES

This application is a continuation-in-part of (1) Application Ser. No. 431,297 filed Jan. 7th, 1974 now U.S. Pat. No. 3,959,486 which is a continuation of Application Ser. No. 145,897, filed May 21, 1971, now abandoned; and of (2) Application Ser. No. 332,517, filed Feb. 14, 1973 now abandoned.

This invention relates to new alkanolamine derivatives which possess β-adrenergic blocking activity as demonstrated by the inhibition of isoprenaline-induced tachycardia in cats.

According to the invention there is provided a new alkanolamine derivative selected from the group consisting of compounds of the formula:

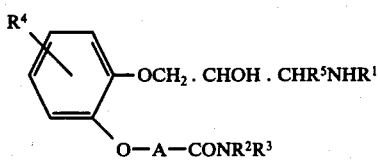

wherein $R^1$ is hydrogen, or unsubstituded alkyl, hydroxyalkyl, cycloalkyl or alkenyl each of up to 6 carbon atoms, or alkyl of up to 6 carbon atoms substitued by phenyl, phenoxy, lower-alkoxy-substituted-phenyl or lower-alkoxy-substituted- phenoxy; wherein $R^2$ is hydrogen or alkyl of up to 6 carbon atoms and $R^3$ is hydrogen, or alkyl, hydroxyalkyl or alkoxy- alkyl each of up to 10 carbon atoms, or cycloalkyl or alkenyl each of up to 6 carbon atoms, or phenylalkyl of up to 12 carbon atoms; or wherein $-NR^2R^3$ is pyrrolidino, piperidino or morpholino; wherein $R^4$ is hydrogen, or halogen, or alkyl, alkenyl, alkylthio, alkoxy, alkenyloxy or halogenoalkyl each of up to 6 carbon atoms, or phenylalkoxy of up to 10 carbon atoms, or hydroxy; wherein $R^5$ is hydrogen or alkyl of up to 6 carbon atoms; and wherein A is straight-or branched-chain alkylene of up to 4 carbon atoms; and the non-toxic, pharmaceutically-acceptable acid-addition salts of said compounds.

It is to be understood that the alkanolamine derivatives of the invention possess an asymmetric carbon atom, namely the carbon atom of the —CHOH— group in the alkanolamine side-chain, and they can therefore exist in racemic and optically-active enantiomorphic forms. It is to be understood that this invention encompasses the racemic form of the alkanolamine derivatives and any enantiomorphic form which possesses β-adrenergic blocking activity. It is further to be understood that β-adrenergic blocking activity usually predominates in that enantiomorphic form which has the "S" absolute configuration of the said —CHOH— group.

$R^1$ may be, for example, hydrogen, methyl, ethyl, n-propyl, isopropyl, n-butyl, s-butyl, t-butyl, n-hexyl, 2-hydroxy-1-methylethyl, 2-hydroxy-1,1-dimethylethyl, cyclo-propyl, cyclobutyl, cyclopentyl, cyclohexyl, allyl, 1-methyl-2-phenoxyethyl, 1,1-dimethyl-2-phenylethyl, 1-methyl-3-phenylpropyl or 2-(3,4-dimethoxyphenyl)ethyl. Preferably $R^1$ contains an alkyl part of 3 or 4 carbon atoms which is branched at the α-carbon atom.

$R^2$ may be, for example, hydrogen, methyl, ethyl or n-propyl.

$R^3$ may be, for example, hydrogen, methyl, ethyl, n-propyl, isopropyl, n-butyl, s-butyl, t-butyl, n-pentyl, isopentyl, n-hexyl, isohexyl, n-heptyl, n-nonyl, 2-hydroxyethyl, 3-hydroxypropyl, 2-hydroxy-1-methylethyl, 2-hydroxy-1,1-dimethylethyl, 2-methoxyethyl, 3-methoxypropyl, cyclopropyl, cyclobutyl, cyclopentyl, cyclohexyl, allyl, benzyl, phenethyl or 1,1-dimethyl-2-phenylethyl.

$R^4$ may be, for example, hydrogen, fluorine, chlorine, bromine, iodine, methyl, ethyl, n-propyl, allyl, methylthio, methoxy, isopropoxy, allyloxy, trifluoromethyl, benzyloxy or hydroxy.

$R^5$ may be, for example, hydrogen or methyl.

A may be, for example, methylene, ethylene, trimethylene or ethylidene.

Suitable non-toxic pharmaceutically-acceptable acid-addition salts of the alkanolamine derivatives of the invention are, for example, salts derived from inorganic acids, for example hydrochlorides, hydrobromides, phosphates or sulphates, or salts derived from organic acids, for example oxalates, lactates, tartrates, acetates, salicylates, citrates, benzoates, β-naphthoates, adipates of 1,1-methylene-bis-(2-hydroxy-3-naphthoates).

A preferred alkanolamine of the invention is selected from the group consisting of compounds of the formula:

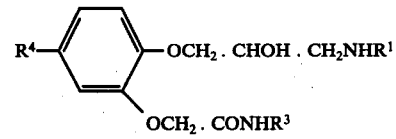

wherein $R^1$, $R^3$ and $R^4$ have the meanings stated above, and the non-toxic, pharmaceutically-acceptable acid-addition salts thereof. Of these, preferred compounds are those wherein $R^1$ is isopropyl, t-butyl or 2-hydroxy-1,1-dimethylethyl, $R^3$ is hydrogen or alkyl, alkenyl or cycloalkyl each of up to 6 carbon atoms and $R^4$ is hydrogen, hydroxy or alkyl of up to 6 carbon atoms, and especially preferred compounds are those wherein $R^3$ is hydrogen, methyl, ethyl or allyl and $R^4$ is hydrogen. Further preferred compounds are those wherein $R^1$ is isopropyl or t-butyl, $R^3$ is 2-hydroxyethyl, 3-hydroxypropyl, 2-methoxyethyl or 3-methoxypropyl and $R^4$ is hydrogen.

Specific alkanolamine derivatives of the invention are, for example, those compounds hereinafter particularly described in Examples 1 to 22. Of these, particularly preferred compounds with respect to their high biological activity are 1-isopropylamino-3-(o-carbamoylmethoxyphenoxy)propan-2-ol; 1-isopropylamino-'-(o-N-methylcarbamoylmethoxyphenoxy)propan-2-ol; 1t-butylamino-3-(o-carbamoylmethoxyphenoxy)propan-2-ol; 1-t-butylamino-3-(o-N-methylcarbamoylmethoxyphenoxy)propan-2-ol; 1-isopropylamino-3-(o-N-allylcarbamoylmethoxyphenoxy)propan-2-ol; 1-t-butylamino-3-(o-N-allylcarbamoylmethoxyphenoxy)propan-2-ol; 1-isopropylamino-3-(o-N-ethylcarbamoylmethoxyphenoxy)propan-2-ol; 1-t-butylamino-3-(o-N-ethylcarbamoylmethoxyphenoxy)-propan-2-ol; 1-isopropylamino-3-(o-N-propylcarbamoylmethoxyphenoxy)propan-2ol; 1-t-butylamino-3-(o-N-propylcarbamoylmethoxyphenoxy)propan-2-ol; 1--o-(N-β-hydroxyethylcarbamoylmethoxy)phenoxy3-isopropylaminopropan-2-ol; 1-o-(N-β-methoxyethylcarbamoylmethoxy)phenoxy-3-isopropylaminopropan-2-ol; 1-o-(N-β-hydroxyethylcarbamoylmethoxy)-phenoxy-3-t-butylaminopropan-2-ol; 1-o-(N-γ-hydroxypropylcarbamoylmethoxy)phenoxy-3-isopropylaminopropan-2-ol; and 1-o-(N-γ-hydroxypropyl-carbamoylmethoxy)phenoxy-3-t-butylaminopropan-2-ol and the non-toxic, pharmaceutically-acceptable acid-addition salts thereof.

The alkanolamine derivatives of the invention may be manufactured by any chemical process known to be suitable for the manufacture of analogous compounds. Such a process may comprise, for example, assembling in sequence, by conventional chemical synthesis, the four groups:

i. a phenoxy group of the formula:

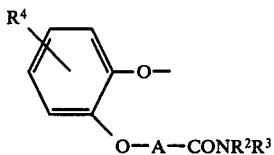

wherein $R^2$, $R^3$, $R^4$ and A have the meanings stated above;

ii. an oxygenated three-carbon group of the formula:

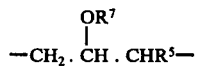

wherein $R^5$ has the meaning stated above and wherein $R^7$ is hydrogen or a protecting group;

iii. an imino group of the formula $-NR^8-$, wherein $R^8$ is hydrogen or a protecting group; and iv. a group of the formula $-R^1$, wherein $R^1$ has the meaning stated above;

whereafter if either or both of $R^7$ and $R^8$ stands for a protecting group, the one or two protecting groups are removed.

The various stages of the assembly may be carried out in any possible order. Thus, for example:

a. A phenol of the formula:

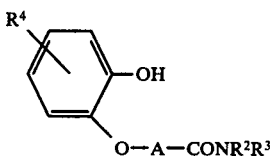

wherein $R^2$, $R^3$, $R^4$ and A have the meanings stated above, which may be obtained from the corresponding hydroxyphenoxy-alkanoic acid by conventional methods of amide formation, may first be reacted with an oxygenated three-carbon derivative, for example a compound of the formula:

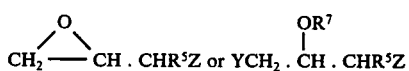

wherein $R^5$ and $R^7$ have the meanings stated above, wherein Y is a displaceable group and wherein Z is hydroxy or a displaceable group. If Z is hydroxy, the intermediate compound obtained is further reacted with a reagent which will replace the hydroxy group Z with a displaceable group Y. The resulting product, which is a compound of the formula:

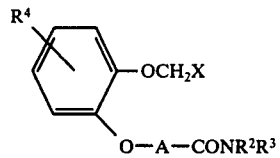

wherein $R^2$, $R^3$, $R^4$ and A have the meanings stated above and wherein X is the group

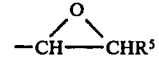

or the group

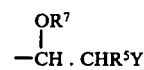

wherein $R^5$, $R^7$ and Y have the meanings stated above, or which may be, when $R^7$ is hydrogen, a mixture of such compounds wherein X has both meanings stated above, is then reacted with an amine of the formula $R^1R^8NH$, wherein $R^1$ and $R^8$ have the meanings stated above.

b. An oxygenated three-carbon derivative, for example a compound of the formula:

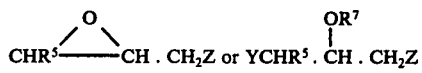

wherein $R^5$, $R^7$, Y and Z have the meanings stated above, is reacted with an amine of the formula $R^1R^8NH$, wherein $R^1$ and $R^8$ have the meanings stated above. If Z is hydroxy the intermediate compound obtained is further reacted with a reagent which will replace the hydroxy group Z with a displaceable group Y. The resulting product, which is a compound of the formula $X^1CHR^5.NR^1R^8$, wherein $R^1$, $R^5$ and $R^8$ have the meanings stated above and wherein $X^1$ is the group

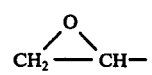

or the group

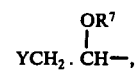

wherein $R^7$ and Y have the meanings stated above, or which may be, when $R^7$ is hydrogen, a mixture of such compounds wherein $X^1$ has both meanings stated above, is then reacted with a phenol of the formula: ,02/0071

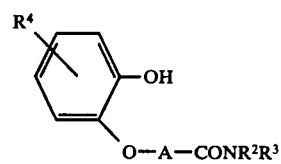

wherein $R^2$, $R^3$, $R^4$ and A have the meanings stated above.

A suitable value for Y, or for Z when it is a displaceable group, is, for example, halogen, for example chlorine or bromine, or sulphonyloxy, for example alkanesulphonyloxy of up to 6 carbon atoms or arenesulphonyloxy of up to 10 carbon atoms, for example methanesulphonyloxy, benzenesulphonyloxy or toluene-p-sulphonyloxy.

A suitable reagent which will replace the hydroxy group Z with a displaceable group Y is, for example, a halogenating agent, for example a thionyl halide, for example thionyl chloride or thionyl bromide, or a sulphonylating agent, for example an lkanesulphonyl halide or an arenesulphonyl halide, for example methanesulphonyl chloride, benzenesulphonyl chloride or toluene-p-sulphonyl chloride.

The reaction involving a phenol reactant may be carried out in the presence of an acid-binding agent, for example an alkali metal hydroxide, for example sodium hydroxide, or an organic base, for example piperidine. Alternatively, an alkali metal derivative of the phenol reactant, for example the sodium or potassium derivative, may be used as starting material. The reaction may be carried out in a diluent or solvent, for example methanol or ethanol, and it may be accelerated or completed by the application of heat, for example by heating to the boiling point of the diluent or solvent.

The reaction involving an amine of the formula $R^1R^8NH$ may be carried out at ambient temperature or it may be accelerated or completed by the application of heat, for example by heating to a temperature of 90°-110° C.; it may be carried out at atmospheric or at an elevated pressure, for example by heating in a sealed vessel; and it may be carried out in an inert diluent or solvent, for example methanol or ethanol, or an excess of the amine of the formula $R^1R^8NH$, wherein $R^1$ and $R^8$ have the meanings stated above, may be used as diluent or solvent.

c. The series of reactions described under (a) or (b) above may be carried out except that an amine of the formula $R^8NH_2$ is used in place of an amine of the formula $R^1R^8NH$, it being understood that when $R^8$ is hydrogen the amine is ammonia. The group $R^1$ may then be inserted as a separate step, for example either by the reaction of the final product from the series of reactions described under (a) or (b) above with a compound of the formula $R^1Y$, wherein $R^1$ and Y have the meanings stated above, or, when $R^8$ is hydrogen, by the reaction under reducing conditions of the final product from the series of reactions described under (a) or (b) above with a carbonyl compound of the formula $R^9.CO.R^{10}$, wherein $R^9$ is alkyl and $R^{10}$ is alkyl, aralkyl, aryloxyalkyl or hydroxyalkyl, or wherein $R^9$ and $R^{10}$ together with the adjacent carbon atom are cycloalkyl, such that $—CHR^9R^{10}$ has the same meaning as is stated above for $R^1$.

A particularly suitable compound of the formula $R^1Y$ is isopropyl bromide. The reaction involving a compound of the formula $R^1Y$ may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenated catalyst, for example palladium or platinum, in an inert diluent or solvent, for example in one or more solvents selected from water, ethanol and an excess of the carbonyl compound used as starting material.

It is to be understood that when in the starting material $R^4$ is halogen, alkenyl, alkylthio, alkenyloxy or aralkoxy, the use of hydrogen and a hydrogenation catalyst is likely to modify the substituent $R^4$, for example by replacement of a chlorine, bromine, iodine or alkylthio substituent by hydrogen, reduction of an alkenyl or alkenyloxy substituent to an alkyl or alkoxy substituent respectively, and hydrogenolysis of an α-arylalkoxy substituent to give the hydroxy substituent.

d. A compound wherein either or both of $R^7$ and $R^8$ is a protecting group may be prepared by the series of reactions described under (a) or (b) or (c) above. Alternatively, a suitable protecting group may be introduced by conventional means into an intermediate compound at any stage preceding the final stage.

A suitable value for $R^7$ when it is a protecting group is, for example, a hydrogenolysable group, for example α-arylalkyl, α-arylalkoxy-carbonyl or α-arylalkoxymethyl, for example benzyl, benzyloxycarbonyl or benzyloxymethyl; or α-aldoxyalkyl (an acetal group), for example tetrahydropyranyl.

A suitable value for $R^8$ when it is a protecting group is, for example, a hyrogenolysable group as defined for $R^7$.

Alternatively, $R^7$ and $R^8$ may be joined together so that one protecting group serves to protect both the oxygen and nitrogen atoms. Such a protecting group may be, for example, a group of the formula $—CHR^6—$, wherein $R^6$ is hydrogen or alkyl of up to 4 carbon atoms or aryl of up to 10 carbon atoms, such that it forms, together with the adjacent oxygen and nitrogen atoms and 2 carbon atoms of the three-carbon group, an oxazolidine nucleus.

The hydrogenolysable protecting group $R^7$ or $R^8$ may be removed, for example, by catalytic hydrogenation, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The α-alkoxyalkyl protecting group $R^7$, or the protecting group $—R^6CH—$ formed by $R^7$ and $R^8$ taken together, may be removed by hydrolysis in the presence of an acid, for example a mineral acid, for example aqueous hydrochloric acid, and the hydrolysis may be carried out at a temperature of up to 100° C.

It is to be understood that a compound wherein $R^3$ or $R^4$ is a functional group may be converted into a different compound wherein $R^3$ or $R^4$ is a different group. Thus, for example, a compound wherein $R^3$ is hydrogen may be converted into the corresponding compound wherein $R^3$ has the same meaning as $R^1$, during the course of the process of the invention described under (a) above which involves an amine of the formula $R^1NH_2$; and a compound wherein $R^4$ is alkenyl, alkenyloxy or α-aralkoxy may be converted to the corresponding compound wherein $R^4$ is, respectively, alkyl, alkoxy or hydroxy, by reaction with hydrogen in the presence of a catalyst, as already stated under (c) above.

Optically-active enantiomorphs of the alkanolamine derivatives of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into a non-toxic, pharmaceutically-acceptable acid-addition salt thereof by interaction with an appropriate acid by conventional means.

The alkanolamine derivative of the invention or a non-toxic, pharmaceutically-acceptable acid-addition salt thereof possesses $\beta$-adrenergic blocking activity and is of value in the treatment or prophylaxis of heart diseases. Furthermore, some such compounds possess selective $\beta$-adrenergic blocking activity. Compounds exhibiting this selective action show a greater degree of specificity in blocking the cardiac $\beta$-receptors than the $\beta$-receptors in peripheral blood vessels and bronchial muscle. Thus, a dose may be selected for such a compound at which the compound blocks the cardiac inotropic and chronotropic actions of a catecholamine, for example isoprenaline, but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the selective compound will substantially inhibit the unwanted stimulatory effects of the bronchodilator on the heart but will not hinder the desirable therapeutic effect of the bronchodilator.

The closest prior art of which Applicants are aware is that of U.S. Pat. No. 3,663,607. Said specification discloses, inter alia, compounds of the formula:

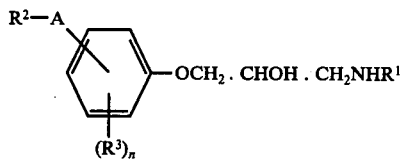

wherein $R^1$ is alkyl or hydroxyalkyl each of up to 6 carbon atoms; wherein $R^2$ is carbamoyl, alkylcarbamoyl or alkenylcarbamoyl wherein the alkyl or alkenyl part each contains up to 6 carbon atoms; wherein A is alkylene of from 1 to 5 carbon atoms or alkenylene of from 2 to 5 carbon atoms; wherein $n$ is 1 or 2; and wherein $R^3$, the values of which may be the same or different when $n$ is 2, is selected from hydrogen, halogen, nitro, hydroxy, cyano, alkyl, alkenyl, alkanoyl and alkoxycarbonyl each of up to 6 carbon atoms, cycloalkyl of up to 8 carbon atoms, alkylthio, alkoxy and alkenyloxy each of up to 5 carbon atoms, phenyl, phenoxy, benzyl, α-phenylethyl and benzyloxy, and alkyl of up to 5 carbon atoms which is substituted by hydroxy, alkoxy of up to 4 carbon atoms or halogen; and the acid-addition salts thereof.

The prior specification is particularly addressed to such compounds wherein the $R^2$—A— substituent is in the para-position relative to the alkanolamine sidechain, and there is only one compound specifically disclosed therein in which the $R^2$—A— substituent is in the ortho-position relative to the alkanolamine sidechain.

The comparison of the $\beta$-adrenergic blocking activity of compounds of the present invention with those of the said prior specification may be carried out using a test standard in the art, namely the inhibition of the tachycardia produced by the injection of 0.2 $\mu$g. per kg. bodyweight of isoprenaline into a chloralose-anaesthetised cat. In this test, $\beta$-adrenergic blocking activity is conveniently expressed as a 50% inhibitory dose (an $ED_{50}$) in $\mu$g./kg. bodyweight on a scale on which the known $\beta$-adrenergic blocking agent propranolol has an $ED_{50}$ of about 60 $\mu$g/kg., and the known cardio-selective $\beta$-adrenergic blocking agent practolol has an $ED_{50}$ of about 200 $\mu$g./kg. On this scale the known ortho-substituted compound of the prior specification, namely 1-o-carbamoylmethylphenoxy-3-isopropylaminopropan-2-ol, has an $ED_{50}$ of 481 $\mu$g./kg., whereas the corresponding compound of the present invention, 1-o-carbamoylmethoxy-phenoxy-3-isopropylaminopropan-2-ol, has an $ED_{50}$ of 58 $\mu$g./kg.

Comparison may also be made between the preferred para-substituted compounds of the prior specification, which have the formula:

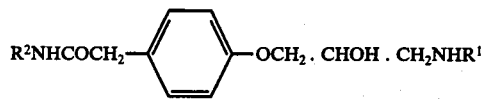

(Compounds A)

and the ortho-substituted compounds of the present invention, which have the formula:

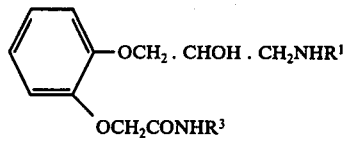

(Compounds B)

The $ED_{50}$ values for all corresponding compounds with identical groups $R^1$ and $R^2$ or $R^3$ are shown in the following table:

| | | $ED_{50}$ ($\mu$g./kg.) | |
|---|---|---|---|
| $R^1$ | $R^2$ or $R^3$ | Compound A | Compound B |
| isopropyl | H | 96 | 58 |
| t-butyl | H | 136 | 11 |
| isopropyl | methyl | 335 | 20 |
| isopropyl | isopropyl | 225 | 200 |
| isopropyl | n-butyl | 606 | 143 |
| isopropyl | allyl | 1470 | 34 |

Other highly active compounds of the present invention which have no exactly corresponding compound in the prior specification have activities shown in the following table:

| R¹ | R³ | ED₅₀(μg./kg.) |
|---|---|---|
| t-butyl | methyl | 14 |
| 2-hydroxy-1,1-dimethylethyl | methyl | 30 |
| isopropyl | ethyl | 68 |
| t-butyl | ethyl | 18 |
| t-butyl | allyl | 27 |
| isopropyl | 2-hydroxyethyl | 9 |
| t-butyl | 2-hydroxyethyl | 40 |
| isopropyl | 3-hydroxypropyl | 47 |
| t-butyl | 3-hydroxypropyl | 74 |
| isopropyl | 2-methoxyethyl | 27 |

It is apparent that the preferred compounds of the present invention are considerably more active as β-adrenergic blocking agents than the closest prior art compounds.

According to a further feature of the invention there is provided a pharmaceutical composition comprising as active ingredient at least one alkanolamine derivative of the invention, or a non-toxic, pharmaceutically-acceptable acid-addition salt thereof, in association with a pharmaceutically-acceptable diluent or carrier therefor.

As a suitable composition there may be mentioned, for example, a tablet, capsule, aqueous or oily solution or suspension, emulsion, injectable aqueous or oily solution or suspension, dispersible powder, spray or aerosol formulation.

The pharmaceutical composition of the invention may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; myocardial depressants, for example quinidine; agents used in the treatment of Parkinson's disease, for example benzhexol; cardiotonic agents, for example digitalis preparations; and sympathomimetic bronchodilators, for example isoprenaline, orciprenaline, adrenaline and ephedrine.

When used in the treatment or prophylaxis of heart diseases, for example angina pectrois and cardiac arrhythmias, or in the treatment of hypertension and phaeochromocytoma, in man, it is expected that the alkanolamine derivative would be given to man at a total oral dose of between 25 mg. and 1200 mg. daily, at doses spaced at 6-8 hourly intervals, or at an intravenous dose of between 1 mg. and 25 mg. Preferred oral dosage forms are tablets or capsules containing between 25 and 200 mg., and preferably 50 mg. or 100 mg., of active ingredient. Preferred intravenous dosage froms are sterile aqueous solutions of the alkanolamine derivative or of a non-toxic acid-addition salt thereof, containing between 0.05% and 1% w/v of active ingredient, and more particularly containing 0.2% w/v of active ingredient.

The invention is illustrated but not limited by the following Examples:

EXAMPLE 1

A solution of 2 g. of 1-chloro-3-(o-carbamoylmethoxyphenoxy)propan-2-ol and 15 ml. of isopropylamine in 15 ml. of methanol is heated in a sealed tube at 110° C. for 12 hours. The mixture is evaporated to dryness and the residue is partitioned between 40 ml. of chloroform and 40 ml. of aqueous 2N-hydrochloric acid. The aqueous acidic layer is separated, made alkaline with sodium carbonate and extracted twice with 40 ml. of chloroform each time. The combined extracts are dried and evaporated to dryness and the residue is crystallised from a mixture of benzene and petroleum ether (b.p. 60°-80° C.). There is thus obtained 1-isopropylamino-3-(o-N-isopropylcarbamoylmethoxyphenoxy)propan-2-ol, m.p. 89°-94° C.

The 1-chloro-3-(o-carbamoylmethoxyphenoxy)propan-2-ol used as starting material may be obtained as follows:

A mixture of 1.5 g. of o-hydroxyphenoxyacetamide, 15 ml. of epichlorohydrin and 6 drops of piperidine is heated at 95°-100° C. for 6 hours and then evaporated to dryness. The residual oil consists of 1-chloro-3-(p-carbamoylmethoxyphenoxy)propan-2-ol and is used without further purification.

EXAMPLE 2

A mixture of 3.9 g. of 1-(o-N-methylcarbamoylmethoxyphenoxy)-2,3-epoxypropane and 30 ml. of isopropylamine is heated at 95°-100° C. for 6 hours. The mixture is evaporated to dryness and the residue is partitioned between 50 ml. of chloroform and 50 ml. of aqueous 2N-hydrochloric acid. The aqueous acidic layer is separated, made alkaline with solid sodium carbonate and extracted three times with 50 ml. of chloroform each time. The combined extracts are dried and evaporated to dryness under reduced pressure and the residue is crystallised from ethyl acetate. There are thus obtained 2.8 g. of 1-isopropylamino-3-(o-N-methylcarbamoylmethoxyphenoxy)propan-2-ol, m.p. 117° C.

The 1-(o-N-methylcarbamoylmethoxyphenoxy)-2,3-epoxypropane used as starting material may be obtained as follows:

3 G. of 1,4-benzodioxan-2one are added portion-wise to a stirred, ice-cold, 27% w/v aqueous solution of methylamine, the temperature of the mixture being kept below 10° C., and after addition is complete the mixture is stirred at room temperature for a further 2 hours. The solution is evaporated to dryness under reduced pressure and the residue is crystallised from water. There is thus obtained o-hydroxyphenoxy-N-methylacetamide, m.p. 149°-150° C.

The o-hydroxyphenoxy-N-methylacetamide is dissolved in a solution of 0.6 g. of sodium hydroxide in 20 ml. of water, 20 ml. of epichlorohydrin are added and the mixture is stirred at room temperature for 17 hours. 20 Ml. of chloroform are then added and the organic layer is separated, washed with water and evaporated to dryness. There is thus obtained 1-(o-N-methylcarbamoylmethoxyphenoxy)-2,3-epoxypropane as an oil which is used without further purification.

EXAMPLE 3

The process described in Example 2 is repeated except that the appropriate 1-(o-carbamoylmethoxyphenoxy)-2,3-epoxypropane is used in place of 1-(o-N-methylcarbamoylmethoxyphenoxy)-2,3-epoxypropane, and there are thus obtained the compounds described in the following table:

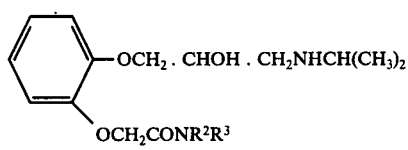

| R² | R³ | m.p. (° C.) | crystallisation solvent |
|---|---|---|---|
| H | H | 108–109 | benzene/petroleum ether (b.p. 60–80° C.) |
| H | ethyl | 97–98 | benzene/petroleum ether (b.p. 60–80° C.) |
| H | n-butyl | 83–84 | ethyl acetate/petroleum ether (b.p. 60–80° C.) |
| H | cyclopentyl | 72–74 | benzene/petroleum ether (b.p. 60–80° C.) |
| H | cyclohexyl | 92–94 | benzene |
| H | allyl | 86 | benzene/petroleum ether (b.p. 60–80° C.) |
| H | benzyl | 84–86 | benzene/petroleum ether (b.p. 60–80° C.) |
| ethyl | ethyl | 55–58 | benzene/petroleum ether (b.p. 60–80° C.) |
| pentamethylene | | hydrogen oxalate 98–100 | acetone |

The 1-(o-carbamoylmethoxyphenoxy)-2,3-epoxypropane derivatives used as starting materials may be obtained from the corresponding phenol and epichlorohydrin by a similar process to that described in the last paragraph of Example 2. The phenols are themselves novel compounds, and these may be obtained by a similar process to that described in the second part of Example 2 from 1,4-benzodioxan-2-one and the appropriate amine. The novel phenols are characterised by the melting points shown in the following table:

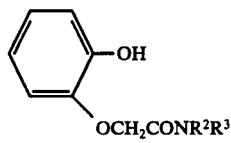

| R² | R³ | m.p. (° C.) |
|---|---|---|
| H | H | 128–129 |
| H | ethyl | 138–139 |
| H | n-butyl | 96–98 |
| H | cyclopentyl | 97–98 |
| H | cyclohexyl | 110–112 |
| H | allyl | 99–100 |
| H | benzyl | 145 |
| ethyl | ethyl | 66–68 |
| pentamethylene | | 93–95 |

EXAMPLE 4

The process described in Example 2 is repeated except that the appropriate amine is used in place of isopropylamine. There are thus obtained the compounds described in the following table:

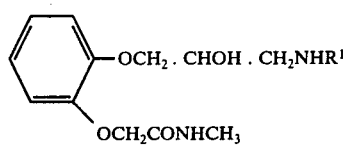

| R¹ | m.p. (° C.) | crystallisation solvent |
|---|---|---|
| H | 88–90* | benzene/petroleum ether (b.p. 60–80° C.) |
| methyl | 97–100* | ethyl acetate/petroleum ether (b.p. 60–80° C.) |
| s-butyl | 98–100 | benzene/petroleum ether (b.p. 60–80° C.) |
| t-butyl | 96–97 | benzene/petroleum ether (b.p. 60–80° C.) |
| n-hexyl | 87 | ethyl acetate |
| allyl | 92–93 | benzene |
| 2-hydroxy-1,1-dimethylethyl | 98–101 | benzene/petroleum ether (b.p. 60–80° C.) |
| 2-(3,4-dimethoxyphenyl)ethyl | oil** | — |

*An aqueous solution of ammonia or methylamine is used and the reaction is carried out at room temperature.
**A solution of 2-(3,4-dimethoxyphenyl)ethylamine in methanol is used and the reaction is carried out at reflux temperature.

The process described above is repeated except that the appropriate amine and the appropriate 1-(o-carbamoylmethoxyphenoxy)-2,3-epoxypropane are used as starting materials, and there are thus obtained:

1-t-butylamino-3-(c-carbamoylmethoxyphenoxy)propan-2-ol;

1-t-butylamino-3-(o-N-allylcarbamoylmethoxyphenoxy)propan-2-ol; and 1-(2-hydroxy-1,1-dimethylethylamino)-3-(o-N-allylcarbamoylmethoxyphenoxy)propan-2-ol, all of which are oils from which no crystalline derivative has been obtained.

EXAMPLE 5

The process described in Example 2 is repeated except that 1-(4-bromo-2-N-methylcarbamoylmethoxyphenoxy)-2,3-epoxypropane is used as starting material in place of 1-(o-N-methylcarbamoylmethoxyphenoxy)-2,3-epoxypropane. There is thus obtained 1-isopropylamino-3-(4-bromo-2-N-methylcarbamoylmethoxyphenoxy)propan-2-ol, m.p 130°–132° C. (crystallised from ethyl acetate).

The 1-(4-bromo-2-N-methylcarbamoylmethoxyphenoxy)-2,3-epoxypropane used as starting material may be obtained as follows:

A solution of 0.55 ml. of bromine in 10 ml. of glacial acetic acid is added to a stirred, ice-cooled, fine suspension of 1.7 g. of o-hydroxyphenoxyacetic acid in 25 ml. of glacial acetic acid, and the mixture is stirred at room temperature for 20 hours and then poured into 300 ml. of water. The aqueous suspension is extracted three times with 200 ml. of chloroform each time and the combined chloroform extracts are dried and evaporated to dryness under reduced pressure. The residue is crystallised from water and there is thus obtained 5-bromo-2-hydroxyphenoxyacetic acid, m.p. 160°–162° C.

The above-mentioned 5-bromo-2-hydroxyphenoxyacetic acid is heated at about 180° C. until bubbling ceases. The product is cooled and the solid residue is crystallised from cyclohexane. There is thus obtained 6-bromo-1,4-benzodioxan-2-one, m.p. 77° –80° C.

This product is reacted with methylamine by a similar process to that described in the second part of Example 2 and there is thus obtained 5-bromo-2-hydroxyphenoxy-N-methylacetamide, m.p. 189°–191° C. (crystallised from aqueous ethanol).

This phenolic product is reacted with epichlorohydrin by a similar process to that described in the last part of Example 2, and there is thus obtained 1-(4-bromo-2N-methylcarbamoylmethoxyphenoxy)-2,3-epoxypropane as an oil which is used without further purification.

EXAMPLE 6

The process described in Example 2 is repeated except that 1-(4-benzyloxy-2-N-methylcarbamoylmethoxyphenoxy)-2,3-epoxypropane is used as starting material in place of 1-(o-N-methylcarbamoylmethoxyphenoxy)-2,3-epoxypropane. There is thus obtained 1-isopropylamino-3-(4-benzyloxy-2-N-methylcarbamoylmethoxyphenoxy)propan-2-ol, m.p. 111°–115° C. (crystallised from toluene).

The 1-(4-benzyloxy-2-N-methylcarbamoylmethoxyphenoxy)-2,3-epoxypropane used as starting material may be obtained as follows:

A solution of 3.2 g. of 2-benzoyloxy-5-benzyloxyphenol in 20 ml. of dimethylformamide is added dropwise to a stirred suspension of 0.24 g. of sodium hydride in 10 ml. of dimethylformamide. A solution of 1.7 g. of ethyl bromacetate in 10 ml. of dimethylformamide is then added dropwise and the mixture is stirred at room temperature for 17 hours. 500 Ml. of water are added and the mixture is extracted three times with 200 ml. of ethyl acetate each time. The combined ethyl acetate extracts are washed three times with 400 ml. of water each time, dried and evaporated to dryness. The residual brown oil is partially purified by crystallisation from cyclohexane, and there is thus obtained ethyl 2-benzoyloxy-5-benzyloxyphenoxyacetate, which is used without further purification.

The above-mentioned ethyl -b 2-benzoyloxy-5-benzyloxyphenoxyacetate is stirred for 24 hours with 70 ml. of 30% w/v aqueous methylamine solution. The mixture is evaporated to dryness and the residue is partitioned between 80 ml. of aqueous N-sodium hydroxide solution and 80 ml. of chloroform. The aqueous extract is separated and acidified with concentrated hydrochloric acid, and the acidic mixture is extracted twice with 100 ml. of chloroform each time. The combined chloroform extracts are dried and evaporated to dryness under reduced pressure, and the residue is crystallised from ethyl acetate. There is thus obtained 5-benzyloxy-2-hydroxy-N-methylphenoxyacetamide, m.p. 149°–152° C.

The above-mentioned phenolic product is reacted with epichlorohydrin by a similar process to that described in the last part of Example 2, and there is thus obtained 1-(4-benzyloxy-2-N-methylcarbamoylmethoxyphenoxy)-2,3-epoxypropane as an oil which is used without further purification.

EXAMPLE 7

A solution of 1 g. of 1-chloro-3-(4-methyl-2-N-methylcarbamoylmethoxyphenoxy)propan-2-ol in a mixture of 20 ml. of isopropylamine and 10 ml. of methanol is heated in a sealed tube at 110° C. for 12 hours. The mixture is evaporated to dryness under reduced pressure and the residue is partitioned between 40 ml. of chloroform and 40 ml. of aqueous 2N-hydrochloric acid. The aqueous acidic layer is separated, made alkaline with solid sodium carbonate and extracted twice with 40 ml. of chloroform each time. The combined extracts are dried and evaporated to dryness under reduced pressure and the residue is crystallised from a mixture of ethyl acetate and petroleum ether (b.p. 60°–80° C.). There is thus obtained 1-isopropylamino-3-(4-methyl-2N-methylcarbamoylmethoxyphenoxy)propan-2-ol, m.p. 101°–103°C.

The 1-chloro-3-(4-methyl-2-N-methylcarbamoylmethoxyphenoxy)propan-2-ol used as starting material may be obtained as follows:

2-Hydroxy-N,5-dimethylphenoxyacetamide, m.p. 163°–165° C., is prepared from 2-benzoyloxy-5-methyphenol by a similar process to that described in Exampl 6 for the preparation of 5-benzoyloxy-2-hydroxy-N-methylphenoxyacetamide from 2-benzoyloxy-5-benzyloxyphenol.

A mixture of 1 g. of 2-hydroxy-N,5-dimethylphenoxyacetamide, 10 ml. of epichlorohydrin and 3 drops of piperidine is heated at 95°–100° C. for 6 hours and then evaporated to dryness under reduced pressure. The residue consists of 1-chloro-3-(4-methyl-2-N-methylcarbamoylmethoxyphenoxy)propan-2-ol and is used without further purification.

EXAMPLE 8

A solution of 0.5 g. of 1-allylamino-3-(2-N-methylcarbamoylmethoxyphenoxy)propan-2-ol (Example 4) in 50 ml. of ethanol is shaken with 0.1 g. of a 5% palladium-on-charcoal catalyst in an atomosphere of hydrogen at atmospheric pressure and room temperature until uptake of hydrogen ceases. The mixture is filtered, the filtrate is evaporated to dryness and the residue is crystallised from a mixture of benzene and petroleum (b.p. 60°–80° C.). There is thus obtained 1-n-propylamino-3-(2-N-methyl-carbamoylmethoxyphenoxy)propan-2-ol, m.p. 114°–115°C.

There are similarly obtained 1-isoproylamino-3-(2-N-propylcarbamoylmethoxyphenoxy)propan-2-ol, m.p. 89°–90° C. from 1-isopropylamino-3-(2-N-allycarbamoylmethoxyphenoxy)propan-2ol (Example 3), and 1-isopropylamino-3-(4-hydroxy-2-N-methylcarbamoylmethoxyphenoxy)-propan-2-ol, m.p. 104°–106° C. from 1-isopropylamino-3-(4-benzyloxy-2-N-methylcarbamoylmethoxyphenoxy)propan-2-ol (Example 6).

EXAMPLE 9

The process described in Example 2 is repeated except that 1-(4-methoxy-2-N-methylcarbamoylmethoxyphenoxy)-2,3-epoxypropane is used as starting material in place of 1-(o-N-methylcarbamoylmethoxyphenoxy)-2,3-epoxypropane. There is thus obtained 1-isopropylamino-3-(4-methoxy-2-N-methylcarbamoylmethoxyphenoxy)propan-2-ol, m.p. 80°–82° C. (crystallised from a mixture of ethyl acetate and petroleum ether, b.p. 60°–80° C.).

The 1-(4-methoxy-2-N-methylcarbamoylmethoxyphenoxy)-2,3-epoxypropane used as starting material may be obtained by a similar process to that described in the second, third and fourth parts of Example 6, except that 2-benzoyloxy-5-methoxyphenol is used in place of 2-benzoyloxy-5-benzyloxyphenol. The 2-hydroxy-5-methoxy-N-methylphenoxyacetamide obtained as intermediate has m.p. 136°–138° C. (crystallised from water).

EXAMPLE 10

The process described in Example 2 is repeated except that 1-(o-N-ethylcarbamoylmethoxyphenoxy)-2,3-epoxypropane and t-butylamine are used as starting materials. The product in free base form, which does not crystallise, is dissolved in ether, an excess of ethereal hydrogen chloride solution is added and the mixture is evaporated to dryness. The residue is boiled with benzene and the mixture is filtered. The solid residue consists of 1-t-butylamino-3-(o-N-ethylcarbamoylmethoxyphenoxy)propan-2-ol hydrochloride, m.p. 152° C.

EXAMPLE 11

The process described in Example 2 is repeated except that 1-[o-(1-N-methylcarbamoylethoxy)phenoxy]-2,3-epoxypropane is used as starting material in place of 1-(o-N-methylcarbamoylmethoxyphenoxy)-2,3-epoxypropane. There is thus obtained 1-isopropylamino-3-[o-(1-N-methyl carbamoylethoxy)-phenoxy]propan-2-ol, m.p. 102°-105° C. (crystallised from ethyl acetate).

The 1-[o-(1-N-methylcarbamoylethoxy)phenoxy]-2,3-epoxypropane used as starting material may be obtained by a similar process to that described in the second and third parts of Example 2, except that 3-methyl-1,4-benzodioxan-2-one is used as starting material in place of 1,4-benzodioxan-2-one. No intermediate product is characterised.

EXAMPLE 12

A solution of 0.8 g. of 1-(N-benzyl-N-isoproylamino)-3-(o-N-methylcarbamoylmethoxyphenoxy)propan-2-ol in 20 ml. of ethanol containing 0.5 ml. of concentrated hydrochloric acid is shaken with 50 mg. of a 5% palladium-on-charcoal catalyst in an atmosphere of hydrogen at atmospheric pressure and laboratory temperature until the uptake of hydrogen ceases. The mixture is filtered and the filtrate is evaporated to dryness. The residue is partitioned between 10 ml. of water and 5 ml. of chloroform and the aqueous layer is separated and basified with solid sodium carbonate. The resulting emulsion is extracted twice with 25 ml. of chloroform each time and the combined extracts are dried and evaporated to dryness. The residue is crystallised from ethyl acetate and there is thus obtained 1-isopropylamino-3-(o-N-methylcarbamoylmethoxyphenoxy)propan-2ol which is identical with the material described in Example 2.

The 1-(N-benzyl-N-isopropylamino)-3-(o-N-methylcarbamoylmethoxyphenoxy)propan-2-ol used as starting material may be obtained, as an oil, by a similar process to that described in Example 2, except that a methanolic solution of N-benzylisopropylamine is used as starting material in place of isopropylamine.

EXAMPLE 13

A mixture of 0.6 g. of 3-amino-1-(o-N-methylcarbamylmethoxyphenoxy)propan-2-ol, 20 ml. of ethanol and 20 ml. of dry acetone is shaken with 0.05 g. of a 5% palladium-on-charcoal catalyst in an atmosphere of hydrogen at a pressure of 50 atmospheres and a temperature of 50° C. for 24 hours. The mixture is filtered and the filtrate is evaporated to dryness. The residue is crystallised from ethyl acetate and there is thus obtained 1-isopropylamino-3-(o-N-methylcarbamoylmethoxyphenoxy)propan-2-ol, which is identical with the material described in Example 2.

EXAMPLE 14

A solution of 2 g. of 1-(o-N-methylcarbamoylmethoxyphenoxy)-2,3-epoxybutane and 25 ml. of isopropylamine in 25 ml. of propanol is heated at 95° -100° C. for 12 hours. The mixture is evaporated to dryness and the residue is partitioned between 50 ml. of chloroform and 50 ml. of aqueous 2N-hydrochloric acid. The aqueous acidic layer is separated, made alkaline with aqueous 2N-sodium hydroxide and extracted twice with 50 ml. of chloroform each time. The combined extracts are dried and evaporated to dryness and the residue is converted into the hydrochloride thereof by conventional means. There is thus obtained 3-isopropylamino-1-(o-N-methylcarbamoylmethoxypheonxy)butan-2-ol hydrochloride, m.p. 184° -186° C. (crystallised from a mixture of ethanol and ether).

The process described above is repeated except that t-butylamine is used in place of isopropylamine. There is thus obtained 3-t-butylamino-1-(o-N-methylcarbamoylmethoxyphenoxy)butan-2-ol hydrochloride, m.p. 177° -179° C. (crystallised from a mixture of ethanol and ether).

The 1-(o-N-methylcarbamoylmethoxyphenoxy)-2,3-epoxybutane used as a starting material may be obtained as follows:

A mixture of 3,6 g. of N-methyl-o-hydroxyphenoxyacetamide, 3,7 g. of 3-bromo-1,2-epoxybutane and 0.9 g. of sodium hydroxide in 40 ml. of water is stirred for 12 hours. The mixture is extracted twice with 50 ml. of chloroform each time. The combined extracts are dried and evaporated to dryness. The residual oil consists of 1-(o-N-methyl-carbamoylmethoxyphenoxy)-2,3-epoxybutane and is used without further purification.

EXAMPLE 15

The process described in Example 8 is repeated except that 1-t-butylamino-3-(2-N-allylcarbamoylmethoxyphenoxy)propan-2-ol (Example 4) is used as starting material. There is thus obtained 1-t-butylamino-3-(2-N-n-propylcarbamoylmethoxyphenoxy)propan-2-ol as an oil, the structure of which is confirmed by proton magnetic resonance spectroscopy.

EXAMPLE 16

A mixture of 1.7 g. of N-$\beta$-hydroxyethyl-o-hydroxyphenoxyacetamide, 0.4 g. of sodium hydroxide, 20 ml. of epichlorohydrin and 20 ml. of water is stirred vigorously for 16 hours. Chloroform (20 ml.) is added, the mixture is shaken and the chloroform layer is separated, dried and evaporated to dryness. A mixture of the residue and 50 ml. of isopropylamine is heated under reflux for 16 hours and then evaporated to dryness. The residue is partitioned between chloroform and aqueous 2N-hydrochloric acid and the acidic layer is basified with solid sodium carbonate. The mixture is extracted several times with chloroform and the combined chloroform extracts are dried and evaporated at dryness. There is thus obtained as oily residue 1-o-(N-$\beta$-hydroxyethylcarbamoylmethoxy)phenoxy-3-isopropylamino-2-propanol, the structure of which is confirmed by proton magnetic resonance spectroscopy.

The N-$\beta$-hydroxyethyl-o-hydroxyphenoxyacetamide used as starting material may be obtained as follows:

1,4-Benzodioxan-2-one (3 g.) is added in portions to a stirred solution of 1.25 g. of 2-aminoethanol in 20 ml. of methanol which is kept at 10°C., and the mixture is kept at laboratory temperature for 48 hours and then evaporated to dryness under reduced pressure. The solid residue is crystallised from ethyl acetate (100 ml.) and there is thus obtained N-$\beta$-hydroxyethyl-o-hydroxyphenoxyacetamide, m.p. 113°-116°C.

EXAMPLE 17

The process described in Example 16 is repeated except that N-$\beta$-methoxyethyl-o-hydroxyphenoxyacetamide (m.p. 96°–97°C. after crystallisation from water; prepared from 1,4-benzodioxan-2-one and 2-methoxyethylamine by a similar process to that described in the second part of Example 16) is used as starting material in place of N-β-hydroxyethyl-o-hydroxyphenoxyacetamide. There is thus obtained 1-o-(N-β-methoxyethylcarbamoylmethoxy)phenoxy-3-isopropylamino-2-propanol, m.p. 78°–80°C. after crystallisation from a mixture of ethyl acetate and petroleum ether (b.p. 60°–80°C.).

EXAMPLE 18

2-Aminoethanol (80 ml.) is added to a stirred solution of 1,4-benzodioxan-2-one (100 g.) in ethanol (1,500 ml.) at such a rate that the temperature of the mixture does not rise above 30°C. The mixture is then kept for a further 2 hours at laboratory temperature and then for 12 hours at 0°C. The mixture is filtered and the solid residue is crystallised from isopropanol. There is thus obtained N-β-hydroxyethyl-o-hydroxyphenoxyacetamide, m.p. 124°–126°C.

A solution of sodium hydroxide (19.2 g.) in water (1,600 ml.) is added dropwise during 7 hours to a two-phase mixture of the above phenolic compound (101.3 g.), epichlorohydrin (374.4 ml.) and water (160 ml.) which is stirred under an atmosphere of nitrogen, and the mixture is then stirred, still under nitrogen, for a further 17 hours. Chloroform (1,000 ml.) is added and the aqueous layer is separated and washed with chloroform (500 ml.). The combined chloroform solutions are washed twice with aqueous 0.8N-sodium hydroxide solution (200 ml. each time) and twice with water (500 ml. each time), dried over magnesium sulphate and evaporated to dryness under reduced pressure. The residue solidifies on standing and there is thus obtained o-(2,3-epoxypropoxy)phenoxy-N-β-hydroxyethylacetamide, m.p. 52°–54°C.

A mixture of the above epoxy compound (27 g.), isopropylamine (90 g.) and water (190 ml.) is heated under reflux in an atmosphere of nitrogen for 45 minutes, and then evaporated to dryness under reduced pressure. The residue is dissolved in aqueous 2N-hydrochloric acid and the solution is washed twice with chloroform (500 ml. each time) and then basified to pH 8 with aqueous 2N-sodium hydroxide solution. The mixture is extracted twice with ethyl acetate (200 ml. each time), the extract being discarded, and the aqueous solution is then further basified to pH 11 and extracted three times with ethyl acetate (200 ml. each time). The combined extracts are dried over magnesium sulphate and evaporated to dryness, and the residue is crystallised from toluene (80 ml.). There is thus obtained 1-o-(N-β-hydroxyethylcarbamoylmethoxy)phenoxy-3-isopropylamino-2-propanol, m.p. 79°–81°C.

One equivalent of glacial acetic acid is added to a solution of the above compound in acetone, and the mixture is filtered. The solid residue is crystallised from acetone and there is thus obtained 1-o-(N-β-hydroxyethylcarbamoylmethoxy)phenoxy-3-isopropylamino-2-propanol acetate, m.p. 99°C.

EXAMPLE 19

The process described in the third paragraph of Example 18 is repeated except that an equivalent amount of o-(3-chloro-2-hydroxypropoxy)phenoxy-N-β-hydroxyethylacetamide is used in place of the corresponding epoxy compound. There is thus obtained 1-o-(N-β-hydroxyethylcarbamoylmethoxy)phenoxy-'-isopropylamino-2-propanol-2-propanol, m.p. 79°–81°C.

The o-3-chloro-2-hydroxypropoxy)phenoxy-N-β-hydroxyethylacetamide used as starting material may be obtained as follows:

A solution of o-(2,3-epoxypropoxy)phenoxy-N-β-hydroxyethylacetamide (85.1 g.) in chloroform (2,000 ml.) is shaken three times with aqueous 2N-hydrochloric acid (2,000 ml. each time). The combined aqueous acidic solutions are then saturated with sodium chloride and extracted three times with chloroform (3,000 ml. each time). The combined extracts are dried over magnesium sulphate and evaporated to dryness under reduced pressure. The residue, which solidifies on standing, is o-(3-chloro-2-hydroxypropoxy)-phenoxy-N-β-hydroxyethylacetamide, m.p. 84°–85°C.

EXAMPLE 20

A mixture of o-(2,3-epoxypropoxy)phenoxy-N-β-hydroxyethylacetamide (300 mg.), t-butylamine (5 ml.) and n-propanol (10 ml.) is heated under reflux for 90 minutes, kept at laboratory temperature for 48 hours and then evaporated to dryness under reduced pressure. The residue is dissolved in aqueous 2N-hydrochloric acid and the solution is filtered. The filtrate is basified with aqueous 2N-sodium hydroxide solution and extracted with chloroform. The extract is dried and evaporated to dryness and there is thus obtained as oily residue 1-o-(N-β-hydroxyethylcarbamolymethoxy)phenoxy-3-t-butylamino-2-propanol, the structure of which is confirmed by elemental analysis, and proton magnetic resonance and mass spectroscopy.

EXAMPLE 21

A mixture of o-(2,3-epoxypropoxy)phenoxy-N-γ-hydroxypropylacetamide (2.7 g.), isopropylamine (6 ml.) and water (14 ml.) is heated under reflux for 30 minutes and then evaporated to dryness under reduced pressure. The residue is dissolved in aqueous 2N-hydrochloric acid (25 ml.) and the solution is basified to pH 8 with aqueous 2N-sodium hydroxide solution and extracted twice with chloroform (25 ml. each time), the extracts being discarded. The aqueous solution is then basified to pH 11 with aqueous 2N-sodium hydroxide solution and again extracted twice with chloroform (50 ml. each time). The combined chloroform extracts are dried over magnesium sulphate and evaporated to dryness, and the residue is triturated with petroleum ether (b.p. 60°–80°C.). There is thus obtained as solid residue 1-o-(N-γ-hydroxypropylcarbamoylmethoxy)phenoxy-3-isopropylamino-2-propanol, m.p. 52°–54°C.

The o-(2,3-epoxypropoxy)phenyl-N-γ-hydroxypropoxyacetamide used as starting material may be obtained as follows:

A solution of 3-aminopropanol (9 ml.) and 1,4-benzodioxan-2-one (20 g.) in ethanol (150 ml.) is kept at laboratory temperature for 18 hours and then evaporated to dryness under reduced pressure. The residue is crystallised from water and there is thus obtained N-γ-hydroxypropyl-o-hydroxyphenoxyacetamide, m.p. 96°–98°C.

The process described in the second paragraph of Example 18 is repeated except that a solution of 1.92 g. of sodium hydroxide in 150 ml. of water is added to a mixture of 10.125 g. of the above compound, 35.1 ml. of epichlorohydrin and 15 ml. of water. The desired epoxy compound is obtained as an oil which is used without further purification.

EXAMPLE 22

The process described in Example 21 is repeated except that t-butylamine is used in place of isopropylamine. There is thus obtained 1-o-(N-γ-hydroxypropyl-carbamoyl-methoxy)phenoxy-3-t-butylamino-2-propanol, m.p. 64° C. after crystallisation from a mixture of toluene and ether.

What we claim is:

1. An alkanolamine derivative selected from the group consisting of compounds of the formula:

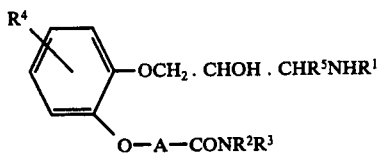

wherein $R^1$ is hydrogen or alkyl, hydroxyalkyl or alkenyl each of up to 6 carbon atoms; wherein $R^2$ is hydrogen or alkyl of up to 6 carbon atoms; wherein $R^3$ is hydrogen, or alkyl, hydroxyalkyl or alkoxyalkyl each of up to 10 carbon atoms, or cycloalkyl or alkenyl each of up to 6 carbon atoms, or phenylalkyl of up to 12 carbon atoms; wherein $R^4$ is hydrogen, or halogen, or alkyl or alkoxy each of up to 6 carbon atoms, or hydroxy; wherein $R^5$ is hydrogen or alkyl of up to 6 carbon atoms; and wherein A is straight-or branched-chain alkylene of up up to 4 carbon atoms; and the non-toxic, pharmaceutically acceptable acid-addition salts thereof.

2. An alkanolamine derivative which is selected from the group consisting of compounds of the formula:

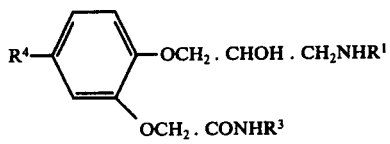

wherein $R^1$, $R^3$ and $R^4$ have the meanings stated in claim 1, and the non-toxic, pharmaceutically-acceptable acid-addition salts thereof.

3. An alkanolamine derivative as claimed in claim 1 selected from the group consisting of 1-t-butylamino-3-(o-N-methylcarbamoylmethoxyphenoxy)propan-2-ol and a non-toxic, pharmaceutically-acceptable acid-addition salt thereof.

* * * * *